United States Patent [19]

Scott

[11] 4,087,517

[45] * May 2, 1978

[54] METHOD OF DRY LUBRICATING THE SKIN

[75] Inventor: Howard L. Scott, Philadelphia, Pa.

[73] Assignees: Charles L. Wragg, Jr.; Fabalon, Inc.; Beverly Wragg; Karen & Wendy Scott Trust, all of Philadelphia, Pa. ; part interest to each

[*] Notice: The portion of the term of this patent subsequent to Jan. 13, 1993, has been disclaimed.

[21] Appl. No.: 648,262

[22] Filed: Jan. 12, 1976

Related U.S. Application Data

[63] Continuation-in-part of Ser. No. 516,817, Oct. 21, 1974, Pat. No. 3,932,614, which is a continuation-in-part of Ser. No. 230,487, Feb. 2, 1972, abandoned.

[51] Int. Cl.$^2$ .................. A61K 7/00; A61K 7/035; A61K 7/48; A61K 31/74
[52] U.S. Cl. .................................. 424/69; 424/78; 424/83
[58] Field of Search .................. 424/69, 71, 73, 78, 424/83

[56] References Cited

U.S. PATENT DOCUMENTS

| 3,340,152 | 9/1967 | Hotko | 264/127 |
|---|---|---|---|
| 3,532,782 | 10/1970 | Hartwimmer | 264/117 |
| 3,568,685 | 3/1971 | Scott | 424/71 |
| 3,932,614 | 1/1976 | Scott | 424/69 X |
| 3,949,764 | 4/1976 | Scott | 424/81 |

OTHER PUBLICATIONS

DuPont, Teflon, Booklet Polychemicals Dept. DuPont Co., Wilmington, Del., 1955, pp. 7, 15-18, 43, 44, 53, 59.
Sagarin, Cos. Sci. & Tech., Intersci. Pub. N.Y., 1957, pp. 99 -106, 223-228, 867-870.

*Primary Examiner*—Albert T. Meyers
*Assistant Examiner*—A. P. Fagelson
*Attorney, Agent, or Firm*—Arthur A. Jacobs

[57] ABSTRACT

The method and means of dry lubricating the skin of human and animal by applying a dry lubricating powders of perfluorocarbon and or fluoropolymer resins, said lubricating powders being inert to human and animal skin tissue, nonagglomerative, and sized to fit smoothly within the crease lines of human and animal skin tissue.

1 Claim, No Drawings

METHOD OF DRY LUBRICATING THE SKIN

This application is a continuation-in-part of co-pending application Ser. No. 516,817, filed Oct. 21, 1974, now U.S. Pat. No. 3,932,614, which is itself a continuation-in-part of application Ser. No. 230,487, filed Feb. 2, 1972, now abandoned.

In accordance with the present invention, an effective lubricating of the skin can take place by sprinkling or rubbing thereon an effective amount of resinous perfluorocarbon dry powder within the crease line of the human or animal skin tissue. These perfluorocarbon resins have a molecular weight of between about 1,000,000 and about 10,000,000 and a viscosity greater than $10^{10}$ poises at 300° C. The amount used may vary widely depending on the type and condition of the skin but may be easily determined by the individual requirements of each user.

The perfluorocarbon resins falling within the scope of this invention include the homopolymer of hexafluoropropylene having the formula

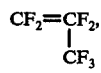

the homopolymer of tetrafluoroethylene having the formula $CF_2=CF_2$, and the co-polymer of tetrafluoroethylene and hexafluoropropylene having the general formula

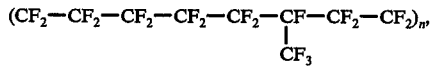

the resins further have a specific gravity of about 2.18 to 2.24, and a melting point of over 500° F.

These resins will not lump or agglomerate either in solutions or on the skin, are generally inert to the actions of body chemistry, whereby they will neither react to body temperature nor break down due to the moisture from the body.

Chlorotrifluoroethylene and fluoropolymer resins have been found to be advantageously used in making dry powder lubricant for the skin in line with this invention.

The various mentioned resins above may be used by themself or in conjunction with Talc or in other composition or diluted in any feasible diluent such as mineral oils, or any of the well known dressing agents.

The following examples are illustrative of the present invention:

1. Body Powder

Perfluorocarbon resins — 95.00%
Talc, Italian type — 5.00
Perfume — q.s.
  Procedure: Mix all ingredients in a ribbon or double cone blender, avoiding excessive agitation.

2. Body Ointment

Petrolatum U.S.P. — 15.00%
Mineral Oil (Light) — 10.00
Fluoropolymer resins — 75.00
Perfume — q.s.
  Procedure:
    1. Warm all ingredients except the last two. Stir until disolved.
    2. Disperse resins.
    3. Added perfume and resins with stirring.

What I claim is:

1. A method of lubricating human and animal skin which comprises applying to said skin (a) lubricatingly effective amount of a lubricating agent selected from the group consisting of polytetrafluoroethylene, polyhexafluoropropylene, polychlorotrifluoroethylene and a copolymer of tetrafluoroethylene and hexafluoropropylene, and (b) a diluent for said lubricating agent, said diluent being selected from the group consisting of talc and oil.

* * * * *